United States Patent
de Groot et al.

(10) Patent No.: US 10,451,413 B2
(45) Date of Patent: Oct. 22, 2019

(54) SURFACE TOPOGRAPHY APPARATUS AND METHOD

(71) Applicant: Zygo Corporation, Middlefield, CT (US)

(72) Inventors: Peter J. de Groot, Middletown, CT (US); Leslie L. Deck, Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 148 days.

(21) Appl. No.: 15/884,951

(22) Filed: Jan. 31, 2018

(65) Prior Publication Data

US 2018/0180412 A1   Jun. 28, 2018

(51) Int. Cl.
*G01B 11/30* (2006.01)
*G06T 7/40* (2017.01)
(Continued)

(52) U.S. Cl.
CPC ........... *G01B 11/30* (2013.01); *G01N 21/952* (2013.01); *G01N 21/956* (2013.01);
(Continued)

(58) Field of Classification Search
CPC .. G01B 11/30; G06T 7/40; G06T 7/49; G06T 2207/30168
(Continued)

(56) References Cited

U.S. PATENT DOCUMENTS

| 5,987,189 A | 11/1999 | Schmucker et al. |
| 6,873,721 B1 | 3/2005 | Beyerer et al. |

(Continued)

FOREIGN PATENT DOCUMENTS

| JP | 2011-043504 | 3/2011 | ........... G01N 21/892 |
| JP | 6040215 | 12/2016 | ............. G01B 11/30 |
| JP | 6119663 | 4/2017 | ........... G01N 21/892 |

OTHER PUBLICATIONS

Beyerer, "Model-based analysis of groove textures with applications to automated inspection of machined surfaces", *Measurement*, vol. 15, pp. 189-199 (1995).

(Continued)

*Primary Examiner* — Hung Nguyen
(74) *Attorney, Agent, or Firm* — Fish & Richardson P.C.

(57) ABSTRACT

An optical method for determining an orientation of surface texture of a mechanical part includes: i) acquiring data for a first areal surface topography image using a surface topography measurement instrument, wherein the first image corresponds to a first field of view of the mechanical part for the surface topography measurement instrument; ii) rotating the mechanical part with respect to a rotation axis provided by a rotatable mount used to secure the mechanical part to provide a second field of view of the mechanical part for the surface topography measurement instrument, wherein the first and second fields of view overlap to provide image information about a common region of the mechanical part; iii) acquiring data for a second areal surface topography image using the surface topography measurement instrument, wherein the second image corresponds to the second field of view; and iv) processing the data from the images.

20 Claims, 5 Drawing Sheets

(51) Int. Cl.
*G01N 21/956* (2006.01)
*G06T 7/49* (2017.01)
*G06T 7/00* (2017.01)
*G01N 21/952* (2006.01)

(52) U.S. Cl.
CPC .............. *G06T 7/0004* (2013.01); *G06T 7/40* (2013.01); *G06T 7/49* (2017.01); *G06T 7/97* (2017.01); *G06T 2207/10072* (2013.01); *G06T 2207/30164* (2013.01); *G06T 2207/30168* (2013.01)

(58) Field of Classification Search
USPC ..................................................... 355/53, 67
See application file for complete search history.

(56) References Cited

U.S. PATENT DOCUMENTS

| | | | |
|---|---|---|---|
| 9,752,868 B2 | 9/2017 | Novak et al. | |
| 9,798,130 B2 | 10/2017 | Dresel et al. | |
| 2010/0149525 A1* | 6/2010 | Lau | G01B 11/002 356/139.03 |
| 2015/0192769 A1* | 7/2015 | Dresel | G02B 21/367 356/450 |

OTHER PUBLICATIONS

Gabryel, "Optimize shaft surface finish for maximum seal performance", *Plant Services* (2002).
Leach, Optical Measurement of Surface Topography, Springer-Verlag, Berlin Heidelberg (2011), Chapter 7 on "Focus Variation Instruments".
Leach, Optical Measurement of Surface Topography, Springer-Verlag, Berlin Heidelberg (2011), Chapter 8 on "Phase Shifting Interferometry".
Leach, Optical Measurement of Surface Topography, Springer-Verlag, Berlin Heidelberg (2011), Chapter 9 on "Coherence Scanning Interferometry".
Leach, Optical Measurement of Surface Topography, Springer-Verlag, Berlin Heidelberg (2011), Chapter 10 on "Digital Holographic Microscope".
Leach, Optical Measurement of Surface Topography, Springer-Verlag, Berlin Heidelberg (2011), Chapter 11 on "Confocal Microscopy".
Leon et al., "Detection of Machine Lead in Ground Sealing Surfaces", *Annals of the CIRP*, vol. 52, pp. 459-462 (Jan. 2003).
"Measurement and Evaluation Method for the Assessment of Lead-Reduced Dynamic Sealing Surfaces," Mercedes-Benz Engineering Standard MBN 31 007-7, edition Apr. 2009 (2009).
Rubber Manufacturers Association, Oil Seal Technical Bulletin, "Shaft Finish Requirements for Radial Lip Seals," RMA OS-1-1 (2004).
Seewig et al., "Lead characterization by an objective evaluation method", *Wear*, vol. 266, No. 5, pp. 530-533 (2009).
Shuster, et al., "Development of the Methodology for 3-D Characterization of Oil Seal Shaft Surfaces", *SAE International* 2002-01-0661 (Mar. 2002).
"Digital Image Correlation", *Wikipedia*, Downloaded on Jan. 31, 2018.
Xin, "Evaluation and characterization of three-dimensional measurement data of technical surfaces with groove textures", MSc thesis from Institute of Measurement and Control Engineering, University of Karlsruhe, Germany (2008) (English translation from original German).
Xin, "Evaluation of Two and a Half Dimensional Surface Data with Form Component and Groove Bands", *Proc. SPIE*, vol. 6503, pp. 65030D-1-65030D-10 (2007).
International Search Report and Written Opinion of the International Searching Authority for International Application No. PCT/US2019/015593 dated May 3, 2019.

* cited by examiner

SURFACE TOPOGRAPHY APPARATUS AND METHOD

FIELD

This disclosure relates to a surface topography apparatus and method for evaluating surface texture direction with respect to a rotation axis.

BACKGROUND

A frequent metrology task in precision engineering is the surface texture analysis of nominally cylindrical areas, including bearing and sealing surfaces on rotating shafts. The machining process can leave signatures, intended or unintended, of the turning, grinding or honing process. These signatures often include groove bands, or more generally, a dominant direction or ensemble of direction for texture marks. The functional behavior of sealing surfaces and bearings can be strongly dependent on the dominant texture direction with respect to the axis of rotation of a machined part. This is for example the case for twist or machining lead angle, hereafter referred to as "lead angle," which characterizes the orientation of the strongest texture direction with respect to the rotation axis. Following common usage in sealing surface characterization, and in analogy with terminology for screws and gears, the lead angle may be calculated from the arctangent of the axial advance of the nominally helical structure of the surface texture during one complete turn divided by the circumference of the one complete turn.

A variety of methods have been developed for measuring the lead angle. For example, a traditional mechanical means for detecting measuring lead angle involves the suspended weight or thread method, as detailed for example in the Rubber Manufacturers Association—Oil Seal Technical Bulletin—Shaft Requirements for Rotary Lip Seals standard ("RMA OS-1-1") from 2004. Other methods rely on mechanically-contacting stylus measurements, as detailed, for example, in "Measurement and Evaluation Method for the Assessment of Lead-Reduced Dynamic Sealing Surfaces," Mercedes-Benz Engineering Standard MBN 31 007-7, edition 2009-04.

SUMMARY

The present disclosures relates to an apparatus and method for determining information about surface texture, such as the lead angle, using a non-contact areal surface topography instrument.

In general, in one aspect, an optical method disclosed for determining an orientation of surface texture of a mechanical part. The method includes: i) acquiring data for a first areal surface topography image using a surface topography measurement instrument, wherein the first image corresponds to a first field of view of the mechanical part for the surface topography measurement instrument; ii) rotating the mechanical part with respect to a rotation axis provided by a rotatable mount used to secure the mechanical part to provide a second field of view of the mechanical part for the surface topography measurement instrument, wherein the first and second fields of view overlap to provide image information about a common region of the mechanical part; iii) acquiring data for a second areal surface topography image using the surface topography measurement instrument, wherein the second image corresponds to the second field of view; and iv) computationally determining information about an orientation of surface texture of the mechanical part relative to the rotation axis based on the data from the first and second overlapping surface topography images.

Embodiments of the method may include any of the following features.

Computationally determining information about the orientation of the surface texture relative to the rotation axis may include: i) analyzing the data from at least one of the surface topography images to determine information about the orientation of the surface texture for the mechanical part with respect to local image coordinates for the surface topography measurement instrument; and ii) determining an orientation of the rotation axis relative to the local image coordinates based on the data from the first and second overlapping surface topography images. Computationally determining the information about the orientation of the surface texture relative to the rotation axis may further include determining the information about the orientation of the surface texture relative to the rotation axis based on the determined orientation of the surface texture for the mechanical part with respect to the local image coordinates and the determined orientation of the rotation axis relative to the local image coordinates.

Determining the orientation of the rotation axis relative to the local image coordinates based on the data from the first and second overlapping surface topography images may include analyzing the data from the first and second overlapping surface topography images to determine a shift in image coordinates from the first field of view to the second field of view for the common region. Determining the shift in image coordinates may include performing an image correlation technique on the data from the first and second overlapping surface topography images to determine a location of the common region of the mechanical part in the local image coordinates for each of the first field of view and the second field of view. The determined orientation of the rotation axis relative to the image coordinates may correspond to an orientation with respect to the image coordinates of an intersection of a plane normal to the rotation axis with a plane defined by the image coordinates. For example, the determined orientation of the rotation axis may be provided by an orientation angle $\gamma$ corresponding to a circumferential direction of the rotation of the part in the image coordinates and defined by $\tan(\gamma) = \Delta x / \Delta y$, where $\Delta x$ and $\Delta y$ correspond to the determined shift in the image coordinates and where the x-axis for the image coordinates is nominally aligned with the rotation axis. In this case, for a global Cartesian coordinate system x', y', and z' where the x'-axis corresponds to the rotation axis and the x'-y' plane is parallel to an x-y image plane for the image coordinates of the surface topography measurement instrument, the orientation angle $\gamma$ provides the angle of rotation of the x'-y' plane from the x-y image plane. Furthermore, in this case, the orientation of the surface texture for the mechanical part with respect to image coordinates may correspond to an angle $\varphi$ of an orientation of grooves on the mechanical part in the x-y image plane, and the information about an orientation of surface texture of the mechanical part relative to the rotation axis may be determined from the orientation angle $\gamma$ and the groove orientation angle $\varphi$. For example, in certain embodiments, the information about an orientation of surface texture of the mechanical part relative to the rotation axis is the lead angle $D\gamma$, which can be derived according to: $D\gamma = 90° - \varphi - \gamma$.

The mechanical part may have a cylindrical shape. Furthermore, the mechanical part may be mounted on the rotatable mount to nominally align the rotation axis of the mount with a symmetry axis of the cylindrical shape of the mechanical part. The surface texture for the mechanical part may correspond to grooves circumscribing the cylindrical shape of the mechanical part.

The computational determining may also include processing the acquired data for at least one of the surface topography images to fit a surface form to the acquired data to determine surface topography variations relative to the fitted surface form. For example, the surface form can be a cylinder. Also, for example, at least one of the areal surface topography images (or each of the areal surface topography images) may be a composite image produced by stitching together multiple areal surface topography images acquired by the surface topography measurement instrument. The method may also further include acquiring data for one or more additional areal surface topography images of the mechanical part, and the determining of the information about the orientation of surface texture of the mechanical part relative to the rotation axis may include averaging information derivable from at least some of the areal surface topography images.

The surface topography measurement system can be a non-contact areal surface topography system. For example, the non-contact areal surface topography system may include an interference microscope, a confocal microscope, a focus variation system, or a fringe projection system. The rotatable mount may include a rotary stage with a chuck for holding the mechanical part.

In another aspect, a method is disclosed for improving, refining, or controlling a production process for a mechanical part. This method includes determining an orientation of surface texture of the mechanical part using the disclosed method above for determining an orientation of surface texture of a mechanical part; and improving, refining, or controlling a production process based on the determined orientation of the surface texture of the mechanical part.

In another aspect, an optical measurement system is disclosed for determining an orientation of surface texture of a mechanical part. The optical measurement system includes a surface topography measurement instrument and a rotatable mount for supporting the mechanical part and adjustably rotating the part about a rotation axis relative to the surface topography measurement instrument. The surface topography measurement instrument is configured to measure a first areal surface topography image corresponding to a first field of view of the mechanical part for the surface topography measurement instrument and a second areal surface topography image corresponding to a second field of view of the mechanical part for the surface topography measurement instrument when the mechanical part is rotated from the first field of view. The first and second fields of view overlap to provide image information about a common region of the mechanical part. The optical measurement system further includes one or more processors coupled to the surface topography measurement instrument to acquire data for the areal surface topography images and computationally determine information about an orientation of surface texture of the mechanical part relative to the rotation axis based on the data from the first and second overlapping surface topography images.

All documents referred to herein are incorporated by reference in their entirety. In case of conflict with the present disclosure, and any document incorporated by reference, the present disclosure controls.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
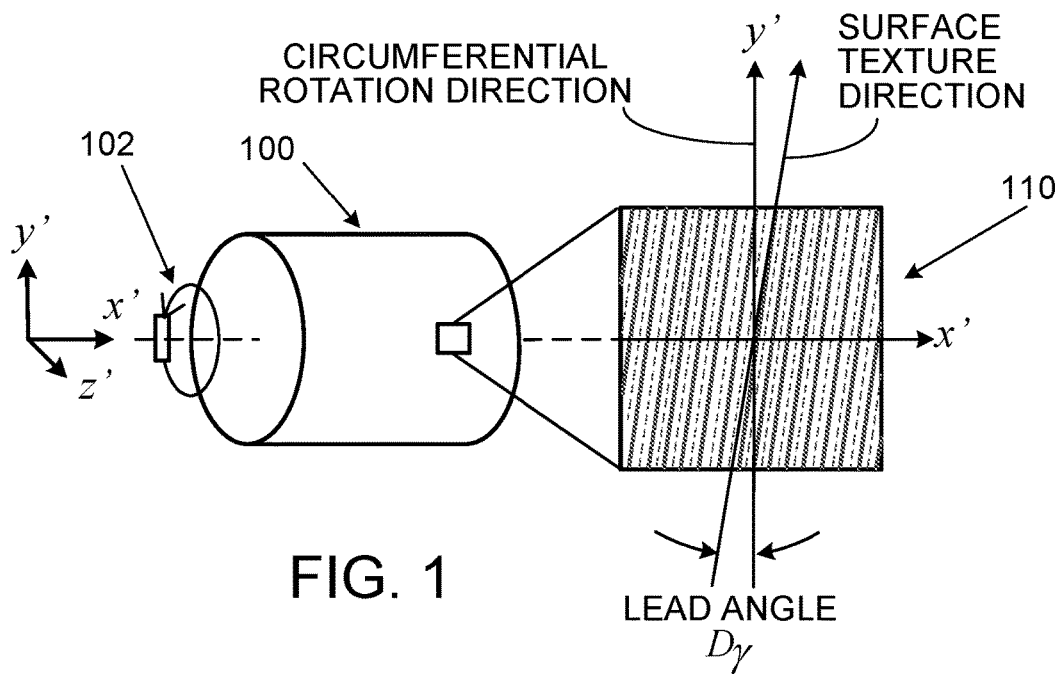
FIG. 1 is a schematic diagram of an optical inspection of cylindrical mechanical part.

FIG. 1 illustrates the concept and geometry of lead angle. A cylindrical part 100 has a rotation axis 102 collinear with a coordinate axis x' for a global Cartesian coordinate system (x', y', z'). The cylindrical part can be, for example, a rotating shaft having bearing and/or sealing surfaces. The part surface can have surface texture corresponding to machining processes (e.g., turning, grinding or honing processes) to complete the shaft. FIG. 1 further illustrates an exploded view of a two-dimensional ("2D") image 110 of the part surface in the right-hand portion of the figure. The 2D-image 110 shows a portion of the cylinder surface orthogonal to the z'-axis, with projection of the y'-axis illustrating the circumferential direction of rotation of the cylindrical part. The 2D image 110 shows a dominant directionality to the surface texture ("surface texture direction"), here illustrated by groove bands, which define a lead angle $D\gamma$ between the surface texture direction and the circumferential rotation direction.

One non-contact method for examining surface texture is optical areal surface topography map, using for example interference microscopy. See, for example, M. Shuster et al., "Development of the Methodology for 3-D Characterization of Oil Seal Shaft Surfaces," SAE International 2002-01-661 (2002). Surface topography mapping provides detailed texture analysis, enabling accurate determination of the dominant surface texture direction, for example by the standardized surface texture direction parameter Std in International Standard ISO 25178-2:2012—"Geometrical product specifications (GPS)—Surface texture: Areal—Part 2: Terms, definitions and surface texture parameters." However, a key problem relates to the orientation of the areal surface topography map with respect to the global coordinates. This is because it is not practical to seek perfect alignment of the topography measuring instrumentation to the global coordinates as part of the measurement setup.

Figure 2:
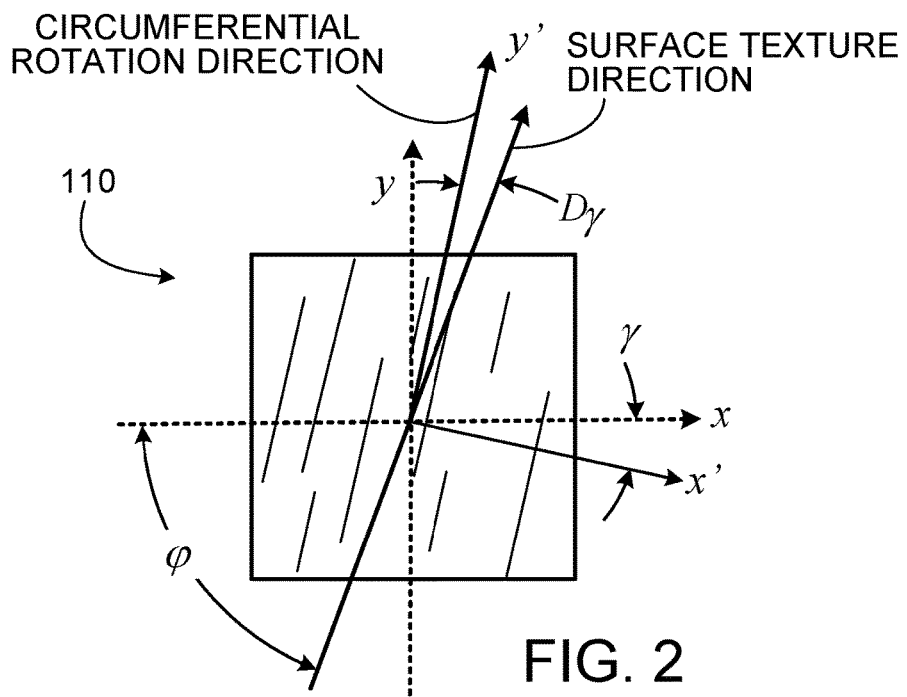
FIG. 2 is a schematic diagram illustrating the relationship between the local Cartesian coordinate system (x, y, z) of a surface topography map for a field of view of the mechanical part and the global Cartesian coordinates (x', y', z').

FIG. 2 illustrates the relationship between the local Cartesian coordinate system (x, y, z) of a surface topography map for a field of view of the mechanical part and the global Cartesian coordinates (x', y', z') 104, where it is assumed that the local x-y plane can be made nominally parallel to the global x'-y' plane, or can be oriented in this way in data processing by adjusting the tip and tilt of the topography map. The angle φ indicates the orientation of the surface texture direction in the local x-y image plane relative to the local x-axis. As noted above, this angle in the local image coordinates can be determined directly from inspection of surface topography map. As also illustrated in FIG. 2, the global y'-axis corresponds to the circumferential rotation direction (because the global x'-axis defines the axis of rotation) and the lead angle Dγ is the angle formed between this circumferential rotation direction and the surface texture direction. The principal source of ambiguity in the measurement of the lead angle Dγ is the unknown orientation angle γ of the topography map about the global z'-axis.

One known method for determining this topography map orientation angle γ is to assume that the rotation axis of the part (corresponding to the global x'-axis) is coincident with the axis of symmetry of the nominally cylindrical part, as determined by a least-squares cylindrical form fit to the areal surface topography map, in local coordinates (x, y, z). The resulting reference surface provides the orientation of the cylinder, and may be subtracted from the topography map to separate the surface texture from the overall form of the part. See Binjian Xin, "Evaluation of two and a half-dimensional surface data with form component and groove bands," Proc. SPIE 6503, Machine Vision Applications in Industrial Inspection XV, 65030D (2007). Based on this approach, there are a wide range of fit and removal strategies to accurately determine the relative orientation of the global coordinates of the part with respect to the local coordinates of the areal surface topography image, followed by an analysis to determine the surface texture direction. See Binjian Xin, "Evaluation and characterization of three dimensional measurement data of technical surfaces with groove textures," MSc thesis from Institute of Measurement and Control Engineering, University of Karlsruhe, Germany 2008 (original in German).

Disclosed herein is directed to a different approach, one which does not require the assumption that the rotation axis of the part (corresponding to the global x'-axis) is coincident with the axis of symmetry of the nominally cylindrical part, thereby reducing constraints on mounting the test part for measurement. In this new approach, the determination of the orientation angle γ of the surface topography image in local coordinates (x, y) with respect to the axis of rotation of the part, corresponding to global x'-axis, is derived from at least two overlapping image data acquisitions resulting from a relative part rotation about the global x'-axis.

Figure 3:
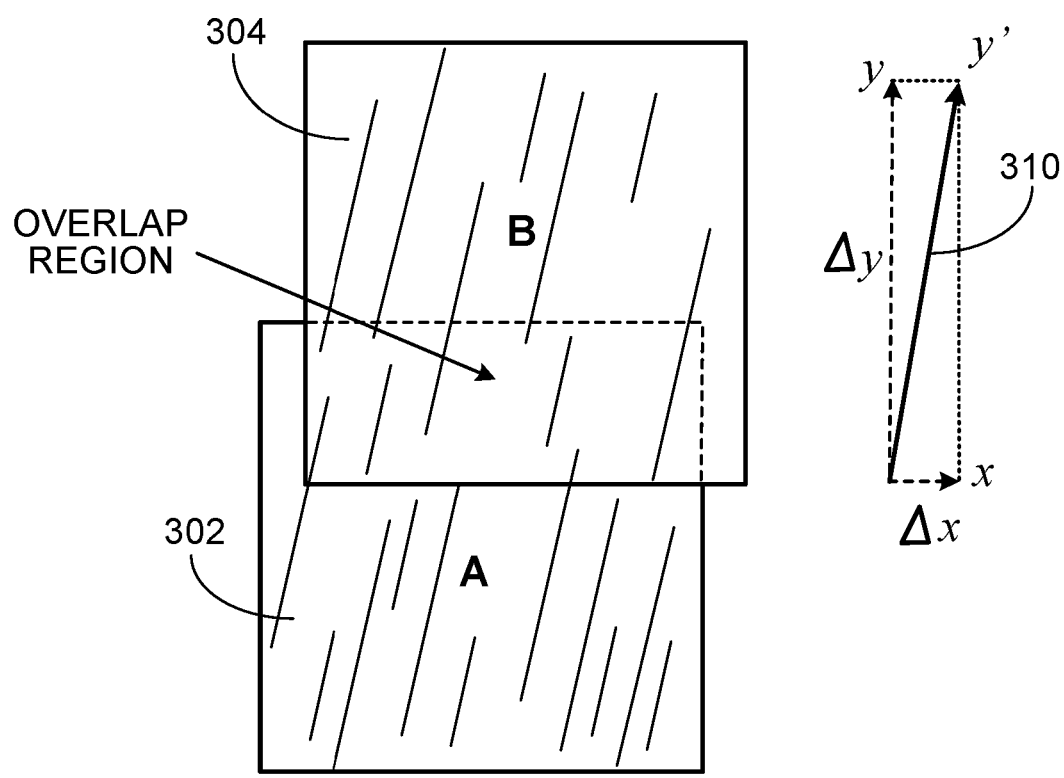
FIG. 3 is a schematic diagram showing how a relative part rotation provides partially overlapping surface topography maps A and B corresponding to neighboring surface areas 302 and 304 shifted with respect to each other along the nominally circumferential direction of rotation 310.

As illustrated in FIG. 3, the relative part rotation provides partially overlapping surface topography maps A and B corresponding to neighboring surface areas 302 and 304 shifted with respect to each other along the nominally circumferential direction of rotation 310, by the projection of the global coordinate y' onto the local coordinate x-y plane. Therefore the overlap region in FIG. 3 represents substantially the same surface area of the part as viewed from two different data acquisitions A and B with a part rotation in between. The shift in Δx, Δy in local topography map coordinates to achieve this overlap defines the angle γ of the cylinder rotation direction according to the equation:

$$\tan(\gamma) = \Delta x / \Delta y \quad (1).$$

The shift Δx, Δy can be determined in any one of several ways, for example, by identifying the change in position in the image coordinates of one or more identifiable landmarks from the overlap region of the part caused by the part rotation. More generally, an image correlation calculation can be applied to the two overlapping images to determine the location of the overlap region and thereby the shift Δx, Δy. See, e.g., https://en.wikipedia.org/wiki/Digital_image_correlation.

After the topography map orientation angle γ and the surface texture direction φ have been determined in the local coordinates, the lead angle Dγ is given by:

$$D\gamma = 90° - \varphi - \gamma \quad (2).$$

This measurement approach has several advantages. First, it is non-contact. Second, unlike the prior art non-contact approach described above, it does not require the assumption that the rotation axis of the part is coincident with the axis of symmetry of the nominally cylindrical part being measured. Third, the approach works well even for large cylinders because the determination of the orientation angle γ based on the shift Δx, Δy of the overlapping images does not require a large field of view. In contrast, when extracting the cylinder orientation by fitting a surface topography map to a cylindrical background, a large field of view is required so that systematic background changes in surface topography caused by the large cylinder are substantial enough to be meaningfully fit to the cylindrical form. Finally, the amount of rotation used to obtain the overlapping images for the rotated part is not required to determine the orientation angle γ and thereafter the lead angle Dγ, although it may be used to provide additional information as described further below.

Figure 4:
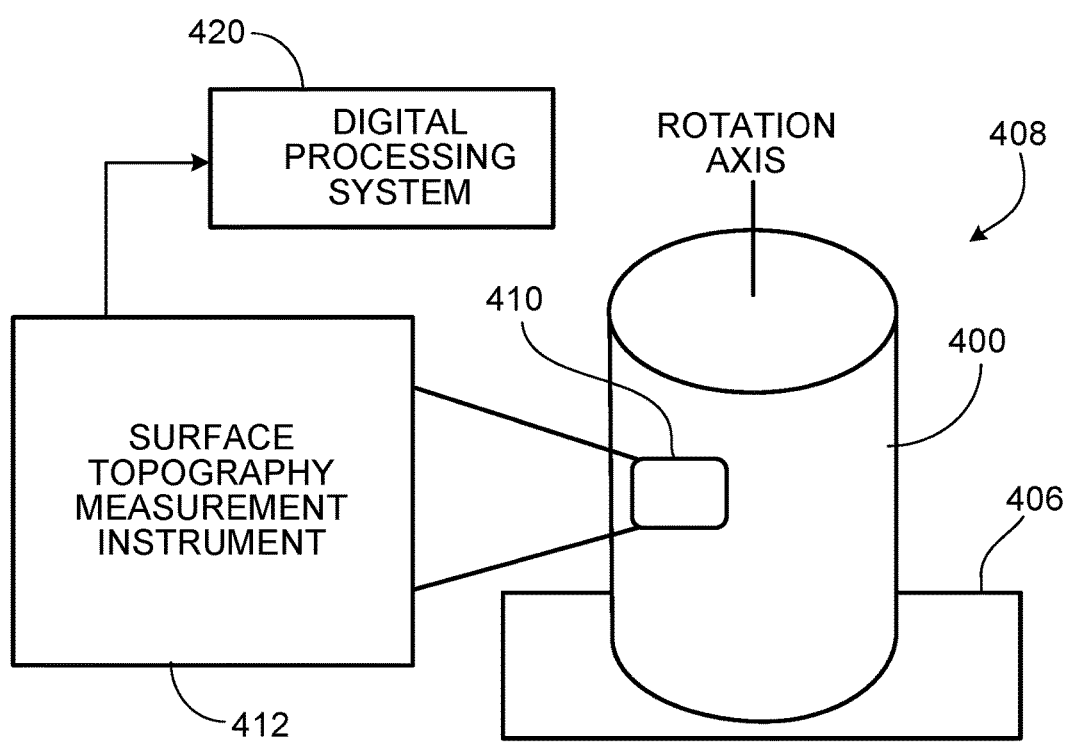
FIG. 4 is a schematic diagram of a measurement system 408 for measuring an orientation of surface texture, e.g., the lead angle, of a mechanical part 400 under test.

FIG. 4 is a schematic diagram of a measurement system 408 for measuring an orientation of surface texture, e.g., the lead angle, of a mechanical part 400 under test. Typically the mechanical part has at least a local surface area that has cylindrical symmetry. The system includes a surface topography measurement instrument 412 for acquiring a surface topography image of the part 400 over a field of view 410 of the part. The system 408 further includes a rotatable mount 406 for positioning the part 400 relative to the surface topography measurement instrument 412. The rotatable mount 406 selectively rotates the part about a rotation axis to provide the surface topography measurement instrument 412 with different fields of view of the part 400. For example, the rotatable mount can be a rotary stage with a chuck for holding the part. A system further includes a digital processing system 420 coupled to the surface topography measurement instrument 412 to receive the surface topography images of the part for different fields of view corresponding to one or more relative rotations of the part about the rotation axis. The digital processing system 420 processes the images to provide a user with information about the orientation of surface texture, e.g., lead angle, of the part.

Optionally, the digital processing system 420 is coupled to the rotatable mount to automate and coordinate the rotation of the part with the surface topography image acquisition. Furthermore, optionally, the digital processing system can receive information about the amount of relative rotation applied to the part for each image acquisition.

The surface topography measuring instrument can be any one of several non-contact areal surface topography systems, including but not limited to an interference microscope (including, e.g., a phase-shifting interference microscope or a coherence scanning interference microscope), a confocal microscope, a focus variation system, a digital holographic microscope, or a fringe projection system, all of which are well-known in the art. See, for example, R. Leach, Ed., *Optical Measurement of Surface Topography*, Springer- Verlag, Berlin Heidelberg (2011), including Chapter 7 on Focus Variation Instruments, Chapter 8 on Phase Shifting Interferometry, Chapter 9 on Coherence Scanning Interferometry, Chapter 10 on Digital Holographic Microscope, and Chapter 11 on Confocal Microscopy. With respect to surface topography instruments based on an interference microscope, the interferometer therein can be, for example, and of the following types: Fizeau, Twyman-Green, Mirau, Linnik, and Michelson.

Figure 5:
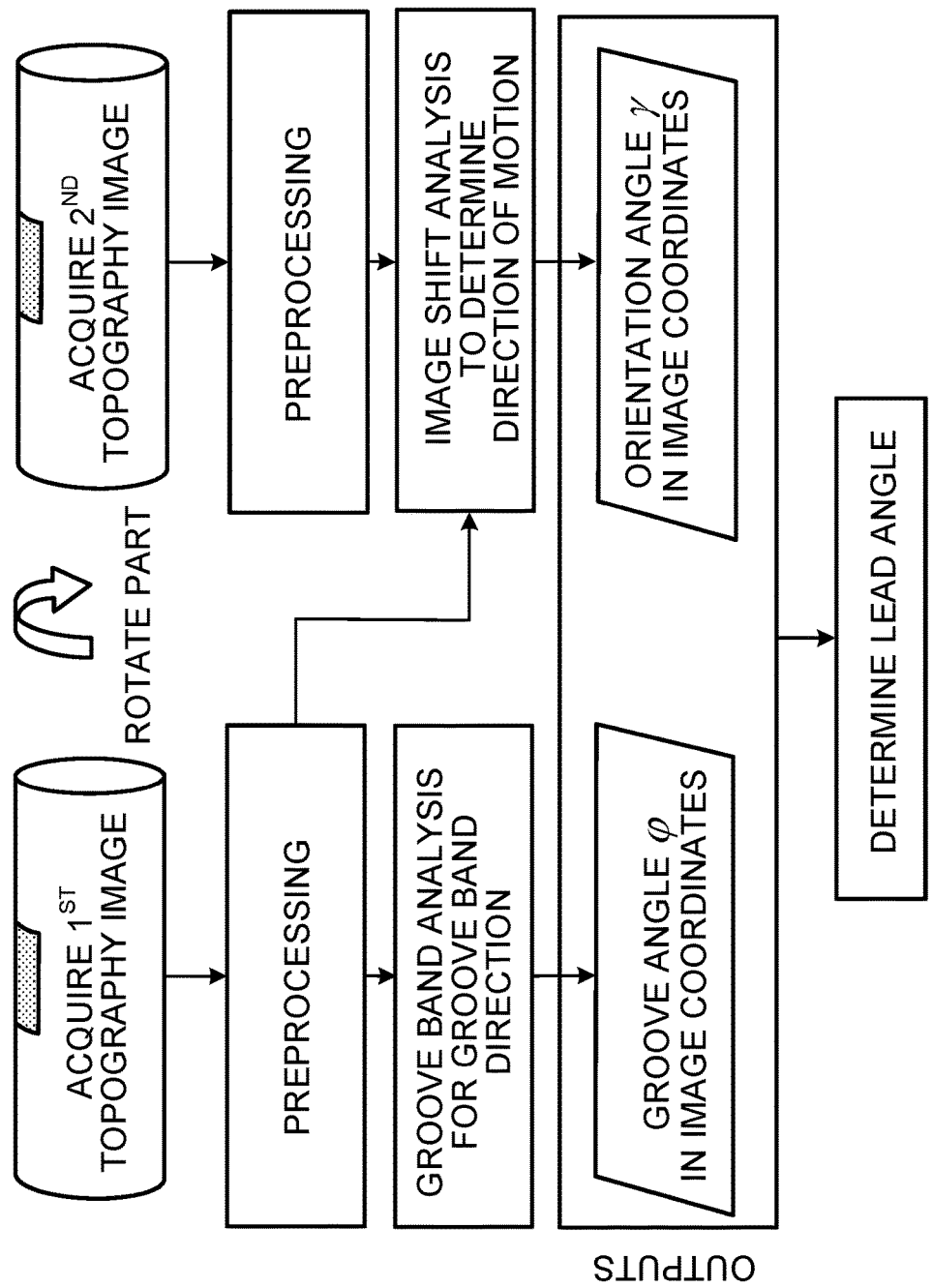
FIG. 5 is a flowchart for an exemplary measurement method as carried out by the measurement system 408.

FIG. 5 is a flowchart for an exemplary measurement method as carried out by the measurement system 408. After the part 400 is mounted on rotatable mount 406, the surface topography measurement instrument 412 acquires a first areal surface topography image of the part 400 for a first field of view. The rotatable mount is then used (whether by manual manipulation or automated control) to rotate the part to provide the surface topography measurement instrument 412 with a second field of view of the part 400 that overlaps with the first field of view. The surface topography measurement instrument 412 then acquires a second areal surface topography image of the part 400 for the second field of view. The digital processing system 420 receives the first and second areal surface topography images of the part for different fields of view from the surface topography measurement instrument 412 and applies any of a number of common preprocessing techniques to each of the images. For example, the images can be pre-processed to remove noise or statistically outlying data or otherwise smooth the image data. Also, for example, the images can be preprocessed to remove tip, tilt, and/or background surface form (such as the cylindrical surface form), so that the subsequent groove band analysis or image shift analysis is more robust. The digital processing system 420 then preforms the groove band analysis on the processed first areal surface topography image to yield the groove angle $\varphi$, which is the orientation of the surface texture direction in the local x-y image plane relative to the local x-axis. The digital processing system 420 also applies the image shift analysis described above to the processed and overlapping areal surface topography images to establish the direction of motion resulting from the rotation in the local image coordinates to thereby yield the orientation angle $\gamma$. Finally, the digital processing system 420 then uses the groove angle $\varphi$ and the orientation angle $\gamma$ to calculate the lead angle $D\gamma$ according to Equation 2 above.

Further embodiments include modifications and variations to the above data acquisition and processing steps. For example, many more than only two areal surface topography images can be acquired and processed. For example, multiple overlapping areal surface topography images can be acquired so as to span a full rotation of the part, and thereby provide as much information as possible about the surface texture of the part. Accordingly, the groove band analysis can be based on information from the multiple images. For example, the groove angle $\varphi$ in local coordinates can be calculated for each image and then averaged to provide a statistically more reliable value for the groove angle and the resulting lead angle. Similarly, the determination of the orientation angle $\gamma$ can be based on information from more than two images. For example, an orientation angle $\gamma$ can be determined from each pair of overlapping images and all such orientation angles can be averaged to provide a statistically more reliable value for the orientation angle and the resulting lead angle. Moreover, for each of the groove angle and the orientation angle, the averaging can include a weighted averages based on other metrics, such as statistical reliability metrics, derived from each images or pair of overlapping images, respectively.

In yet further embodiments, multiple images can be stitched together to provide a composite image with a greater field of view and therefore more information for determining the groove angle $\varphi$ and/or the orientation angle $\gamma$. Such stitching techniques are well known in the image processing prior art, including stitching of surface topography images derived from interference microscopy. See, for example, U.S. Pat. No. 5,987,189 entitled "Method of Combining Multiple Sets of Overlapping Surface-Profile Interferometric Data to Produce a Continuous Composite Map," the contents of which are incorporated herein by reference. Further embodiments can include additional image processing techniques known in the art, such as, for example, the image processing techniques for obtaining composite images disclosed in U.S. Pat. No. 9,798,130 entitled "Measuring Topography of Aspheric and other Non-Flat Surfaces," the contents of which are incorporated herein by reference.

In yet further embodiments, a priori information about the radius of the cylindrical part under inspection and the rotation angle can be used to determine the Ay shift between two overlapping images. This Ay shift can be used together with the Ay shift determine from image correlation to provide a more accurate value of the Ay shift and/or it can be used a reliability check on the result from the image correlation and/or it can be used to speed up the correlation processing be limiting the range of Ay shifts for which a correlation metric is calculated.

Figure 6:
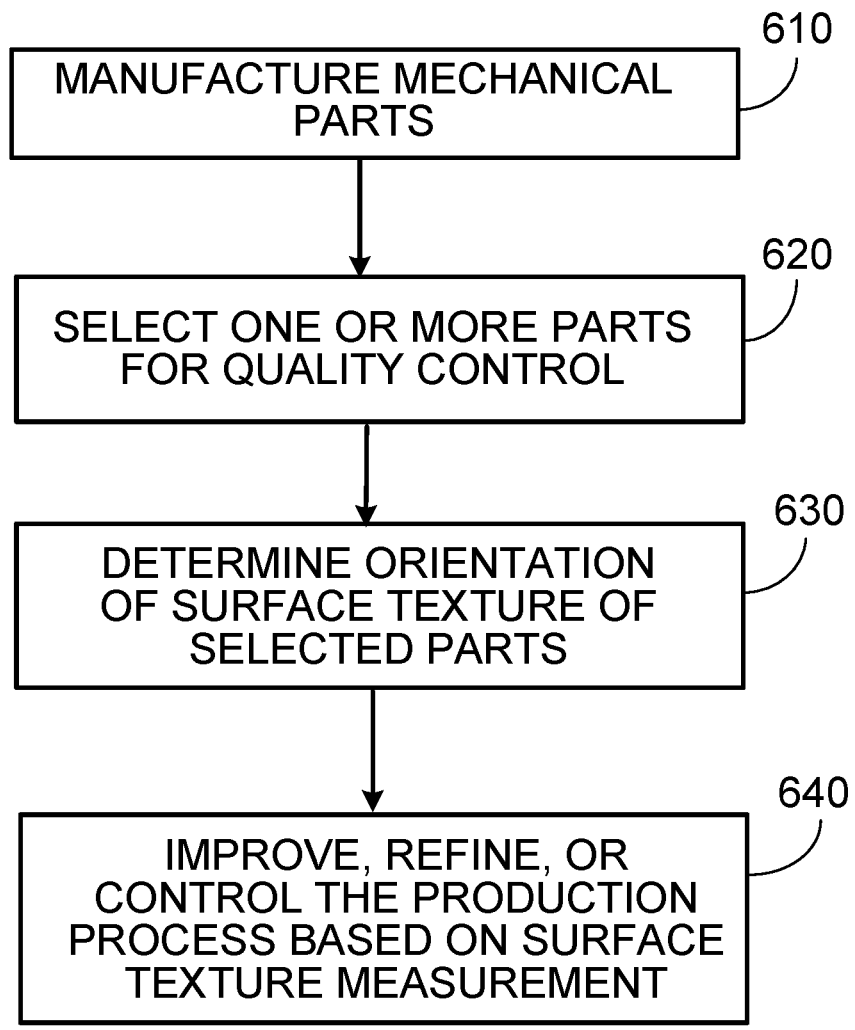
FIG. 6 is a flowchart illustrating a quality control method for a production process.

The methods and systems described herein can be implemented in a production process for making the mechanical part as illustrated, for example, in the flow chart of FIG. 6. In step 610, mechanical parts having a nominally cylindrical areas, including, for example, bearing and sealing surfaces on rotating shafts are manufactured in a repetitive production process. In step 620, one or more of the manufactured parts are selected for quality control. In step 630, the method described above for determining an orientation of surface texture is applied to the selected manufactured part. In step 640, information about the determined orientation of the surface texture is used to improve, refine, or control the production process. For example, the determined orientation of the surface texture for each mechanical part can be compared to a priori design tolerance specifications to determine whether the part should be accepted or not as part of a quality control process. Also, for example, the optical measurement of the orientation of the surface texture can be implemented as an inline or as an off-line step in the production process for the manufactured parts.

Digital Implementations

The features of the data processing described herein can be implemented in digital electronic circuitry, or in computer hardware, firmware, or in combinations of these. The features can be implemented in a computer program product tangibly embodied in an information carrier, e.g., in a machine-readable storage device, for execution by a programmable processor; and features can be performed by a programmable processor executing a program of instructions to perform functions of the described implementations by operating on input data and generating output. The described features can be implemented in one or more computer programs that are executable on a programmable system including at least one programmable processor coupled to receive data and instructions from, and to transmit data and instructions to, a data storage system, at least one input device, and at least one output device. A computer program includes a set of instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Suitable processors for the execution of a program of instructions include, by way of example, both general and special purpose microprocessors one of multiple processors of any kind of computer. Generally, a processor will receive instructions and data from a read-only memory or a random access memory or both. Computers include a processor for executing instructions and one or more memories for storing instructions and data. Generally, a computer will also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks. The processor and the memory can be supplemented by, or incorporated in, ASICs (application-specific integrated circuits).

The features can implemented in a single process or distributed among multiple processors at one or many locations. For example, the features can employ cloud technology for data transfer, storage, and/or analysis.

Scope

It must be noted that as used herein and in the appended claims, the singular forms "a", "an", and "the" include plural referents unless the context clearly dictates otherwise, e.g., when the word "single" is used.

As used herein, the terms "adapted" and "configured" mean that the element, component or other subject matter is designed and/or intended to perform a given function. Thus, the use of the terms "adapted" and "configured" should not be construed to mean that a given element, component, or other subject matter is simply "capable of" performing a given function.

As used herein, the phrases "at least one of" and "one or more of," in reference to a list of more than one entity, means any one or more of the entity in the list of entity, and is not limited to at least one of each and every entity specifically listed within the list of entity. For example, "at least one of A and B" (or, equivalently, "at least one of A or B," or, equivalently, "at least one of A and/or B") may refer to A alone, B alone, or the combination of A and B.

As used herein, the term "and/or" placed between a first entity and a second entity means one of (1) the first entity, (2) the second entity, and (3) the first entity and the second entity. Multiple entity listed with "and/or" should be construed in the same manner, i.e., "one or more" of the entity so conjoined. Other entity may optionally be present other than the entity specifically identified by the "and/or" clause, whether related or unrelated to those entities specifically identified.

While this specification contains many specific implementation details, these should not be construed as limitations on the scope of any inventions or of what may be claimed, but rather as descriptions of features specific to particular embodiments of particular inventions.

Certain features that are described in this specification in the context of separate embodiments can also be implemented in combination in a single embodiment. Conversely, various features that are described in the context of a single embodiment can also be implemented in multiple embodiments separately or in any suitable subcombination.

Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain implementations, multitasking and parallel processing may be advantageous.

A number of embodiments of the invention have been described. Nevertheless, it will be understood that various modifications may be made without departing from the spirit and scope of the invention. Accordingly, other embodiments are within the scope of the following claims.

What is claimed is:

1. An optical method for determining an orientation of surface texture of a mechanical part, the method comprising:
    a. Acquiring data for a first areal surface topography image using a surface topography measurement instrument, wherein the first image corresponds to a first field of view of the mechanical part for the surface topography measurement instrument;
    b. Rotating the mechanical part with respect to a rotation axis provided by a rotatable mount used to secure the mechanical part to provide a second field of view of the mechanical part for the surface topography measurement instrument, wherein the first and second fields of view overlap to provide image information about a common region of the mechanical part;
    c. Acquiring data for a second areal surface topography image using the surface topography measurement instrument, wherein the second image corresponds to the second field of view; and
    d. Computationally determining information about an orientation of surface texture of the mechanical part relative to the rotation axis based on the data from the first and second overlapping surface topography images.

2. The method of claim 1, wherein computationally determining information about the orientation of the surface texture relative to the rotation axis comprises:

a. analyzing the data from at least one of the surface topography images to determine information about the orientation of the surface texture for the mechanical part with respect to local image coordinates for the surface topography measurement instrument; and b. determining an orientation of the rotation axis relative to the local image coordinates based on the data from the first and second overlapping surface topography images.

3. The method of claim 2, wherein computationally determining the information about the orientation of the surface texture relative to the rotation axis further comprises determining the information about the orientation of the surface texture relative to the rotation axis based on the determined orientation of the surface texture for the mechanical part with respect to the local image coordinates and the determined orientation of the rotation axis relative to the local image coordinates.

4. The method of claim 2, wherein determining the orientation of the rotation axis relative to the local image coordinates based on the data from the first and second overlapping surface topography images comprises analyzing the data from the first and second overlapping surface topography images to determine a shift in image coordinates from the first field of view to the second field of view for the common region.

5. The method of claim 4, wherein determining the shift in image coordinates comprises performing an image correlation technique on the data from the first and second overlapping surface topography images to determine a location of the common region of the mechanical part in the local image coordinates for each of the first field of view and the second field of view.

6. The method of claim 5, wherein the determined orientation of the rotation axis is provided by an orientation angle γ corresponding to a circumferential direction of the rotation of the part in the image coordinates and defined by $\tan(\gamma) = \Delta x/\Delta y$, where $\Delta x$ and $\Delta y$ correspond to the determined shift in the image coordinates and where the x-axis for the image coordinates is nominally aligned with the rotation axis.

7. The method of claim 6, wherein for a global Cartesian coordinate system x', y', and z' where the x'-axis corresponds to the rotation axis and the x'-y' plane is parallel to an x-y image plane for the image coordinates of the surface topography measurement instrument, the orientation angle γ provides the angle of rotation of the x'-y' plane from the x-y image plane.

8. The method of claim 7, wherein the orientation of the surface texture for the mechanical part with respect to image coordinates corresponds to an angle γ of an orientation of grooves on the mechanical part in the x-y image plane, and wherein the information about an orientation of surface texture of the mechanical part relative to the rotation axis is determined from the orientation angle γ and the groove orientation angle φ.

9. The method of claim 8, wherein the information about an orientation of surface texture of the mechanical part relative to the rotation axis is the lead angle Dγ according to: Dγ=90°−φ−γ.

10. The method of claim 2, wherein the determined orientation of the rotation axis relative to the image coordinates corresponds to an orientation with respect to the image coordinates of an intersection of a plane normal to the rotation axis with a plane defined by the image coordinates.

11. The method of claim 1, wherein the mechanical part has a cylindrical shape.

12. The method of claim 11, wherein the mechanical part is mounted on the rotatable mount to nominally align the rotation axis of the mount with a symmetry axis of the cylindrical shape of the mechanical part.

13. The method of claim 11, wherein the surface texture for the mechanical part corresponds to grooves circumscribing the cylindrical shape of the mechanical part.

14. The method of claim 1, wherein the computational determining comprises processing the acquired data for at least one of the surface topography images to fit a cylindrical surface form to the acquired data to determine surface topography variations relative to the fitted surface form.

15. The method of claim 1, wherein the surface topography measurement system is a non-contact areal surface topography system comprising an interference microscope, a confocal microscope, a focus variation system, or a fringe projection system.

16. The method of claim 1, wherein the rotatable mount comprises a rotary stage with a chuck for holding the mechanical part.

17. The method of claim 1, further comprising acquiring data for one or more additional areal surface topography images of the mechanical part and wherein the determining of the information about the orientation of surface texture of the mechanical part relative to the rotation axis comprises averaging information derivable from at least some of the areal surface topography images.

18. The method of claim 1, wherein at least one of the areal surface topography images is a composite image produced by stitching together multiple areal surface topography images acquired by the surface topography measurement instrument.

19. A method for improving, refining, or controlling a production process for a mechanical part, the method comprising:

a. determining an orientation of surface texture of the mechanical part using the method of claim 1; and b. improving, refining, or controlling a production process based on the determined orientation of the surface texture of the mechanical part.

20. An optical measurement system for determining an orientation of surface texture of a mechanical part, the system comprising:

a. a surface topography measurement instrument and a rotatable mount for supporting the mechanical part and adjustably rotating the part about a rotation axis relative to the surface topography measurement instrument, b. wherein the surface topography measurement instrument is configured to measure a first areal surface topography image corresponding to a first field of view of the mechanical part for the surface topography measurement instrument and a second areal surface topography image corresponding to a second field of view of the mechanical part for the surface topography measurement instrument when the mechanical part is rotated from the first field of view, c. wherein the first and second fields of view overlap to provide image information about a common region of the mechanical part; and d. one or more processors coupled to the surface topography measurement instrument to acquire data for the areal surface topography images and computationally determine information about an orientation of surface texture of the mechanical part relative to the rotation axis based on the data from the first and second overlapping surface topography images.

\* \* \* \* \*

UNITED STATES PATENT AND TRADEMARK OFFICE
CERTIFICATE OF CORRECTION

PATENT NO. : 10,451,413 B2
APPLICATION NO. : 15/884951
DATED : October 22, 2019
INVENTOR(S) : Peter J. de Groot and Leslie L. Deck It is certified that error appears in the above-identified patent and that said Letters Patent is hereby corrected as shown below:

In the Claims

<u>Column 11</u>
Line 51, in Claim 8, delete "angle $\gamma$" and insert -- angle $\varphi$ --

Signed and Sealed this
Twenty-fourth Day of December, 2019

Andrei Iancu
*Director of the United States Patent and Trademark Office*